(12) United States Patent
McKinnon et al.

(10) Patent No.: US 6,626,913 B1
(45) Date of Patent: Sep. 30, 2003

(54) METHODS, SYSTEMS, AND INSTRUMENTS FOR INSERTING PROSTHETIC IMPLANTS

(75) Inventors: Brian W. McKinnon, Bartlett, TN (US); David C. Kelman, Collierville, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 09/914,498

(22) PCT Filed: Mar. 3, 2000

(86) PCT No.: PCT/US00/05442

§ 371 (c)(1),
(2), (4) Date: Dec. 27, 2001

(87) PCT Pub. No.: WO00/51530

PCT Pub. Date: Sep. 8, 2000

Related U.S. Application Data (60) Provisional application No. 60/122,631, filed on Mar. 3, 1999.

(51) Int. Cl.[7] ................................................. A61B 17/58
(52) U.S. Cl. .............................. 606/99; 606/91; 606/86
(58) Field of Search ............................... 606/91, 99, 92, 606/86, 89, 102; 623/22.11, 22.32

(56) References Cited

U.S. PATENT DOCUMENTS

| | | | |
|---|---|---|---|
| 3,857,389 A | 12/1974 | Amstutz | |
| D290,399 S | 6/1987 | Kitchens | |
| 4,919,679 A | 4/1990 | Averill et al. | |
| 4,993,410 A | 2/1991 | Kimsey | |
| 5,064,427 A | 11/1991 | Burkinshaw | |
| 5,190,549 A | 3/1993 | Miller et al. | |
| 5,190,550 A | 3/1993 | Miller et al. | |
| D337,639 S | 7/1993 | Beckman | |
| D340,979 S | 11/1993 | Hershberger et al. | |
| D347,689 S | 6/1994 | Hershberger et al. | |
| D353,001 S | 11/1994 | Petersen | |
| 5,364,403 A | * 11/1994 | Petersen et al. | ............... 606/91 |
| 5,409,492 A | 4/1995 | Jones et al. | |
| 5,443,471 A | 8/1995 | Swajger | |
| 5,470,336 A | 11/1995 | Ling et al. | |
| 5,476,466 A | 12/1995 | Barrette et al. | |
| 5,534,006 A | 7/1996 | Szabo et al. | |
| 5,540,697 A | 7/1996 | Whitlock | |
| 5,584,837 A | * 12/1996 | Petersen | ..................... 606/91 |
| 5,674,225 A | 10/1997 | Muller | |
| 5,800,546 A | 9/1998 | Marik et al. | |
| 5,849,015 A | 12/1998 | Haywood et al. | |
| 6,113,605 A | * 9/2000 | Storer | ......................... 606/99 |
| 6,238,435 B1 | * 5/2001 | Meulink et al. | ......... 623/22.12 |
| 6,395,005 B1 | * 5/2002 | Lovell | ......................... 606/91 |

FOREIGN PATENT DOCUMENTS

| | | |
|---|---|---|
| DE | 94 18 964 U | 1/1995 |
| EP | 0550118 | 7/1996 |
| FR | 2 615 097 | 11/1988 |
| FR | 2 721 502 A | 12/1995 |
| WO | WO 97/33538 | 9/1997 |
| WO | WO 00/51530 | 9/2000 |

* cited by examiner

*Primary Examiner*—Pedro Philogene
(74) *Attorney, Agent, or Firm*—Kilpatrick Stockton LLP (57) ABSTRACT

An inserter includes a frame having a central bore through which a threaded rod is inserted, the threaded rod being used to secure the inserter to an object such as an implant. A thumbscrew is used to thread the rod into the object. A biasing member is located between the thumbscrew and a slider. A lever on the inserter is provided such that when the lever is closed, the slider is forced toward the thumbscrew, compressing the biasing member and generate opposing forces applied to the thumbscrew and slider. These opposing forces are transferred to the rod and frame and produce a resultant force that causes a compressive force to be exerted between the inserter and object. This resultant force firmly seats the inserter on the object and reduces the possibility that any blows applied to the inserter are diverted to the rod causing the rod to loosen or disengage.

20 Claims, 11 Drawing Sheets

METHODS, SYSTEMS, AND INSTRUMENTS FOR INSERTING PROSTHETIC IMPLANTS

RELATED APPLICATION DATA

This application claims priority to U.S. Application Ser. No. 60/122,631, filed Mar. 3, 1999, and International Application No. PCT/00/05442 filed on Mar. 3, 2000 and published in English as International Publication No. WO 00/51530 on Sep. 8, 2000, the entire contents of which are hereby incorporated by reference.

FIELD OF THE INVENTION

The present invention relates generally to methods, systems, and instruments for inserting prosthetic implants, instruments, and other devices and, more particularly, to methods, systems, and instruments for inserting implants and other instruments into medullary canals of bones.

BACKGROUND OF THE INVENTION

In arthroplasty, a prosthetic implant is often inserted into a medullary canal of a bone. In addition to the implant itself, other instruments or devices may also need to be inserted. Examples of these instruments include broaches, reamers, alignment tools, depth guides, and gauges. Because of medullary and cortical tissue within the bone, insertion of the implant or instrument typically requires the delivery of a force to the implant or instrument in order to drive the implant or instrument to a desired position within the bone. Various methods, systems, and instruments have been devised to assist in the placement of the implant or instrument at the desired position within a bone.

For example, an inserter or impactor is a commonly used device for driving an implant into the medullary canal of a bone. The inserter features a rod that is in some way connected to a frame and which runs through this frame and connects to one end of the implant, as by a threaded end on the rod which is received in a threaded bore in the end of the implant. Additionally, the inserter features a load transfer surface integral to the frame near the end of the rod, which abuts against an impact surface at the end of the implant. The rod is securely connected to the implant in order to apply compression between the inserter and the implant, and more specifically to compress the impact surface of the inserter against the impact surface of the implant. After the inserter has been firmly secured to the implant, a surgeon applies forces to the inserter as with a mallet and these forces are transferred through the inserter frame to the implant to cause the implant to move to the desired location. After the implant has been driven to its desired location, the surgeon disconnects the rod to remove the inserter from the implant.

A difficulty arises during the impaction of an implant in that the mallet blows cause vibrations within the inserter and these vibrations lead to a retraction of the rod from within the implant. As the rod retracts, the compression between the impact surface on the frame of the inserter and the same on the implant is relieved and the inserter becomes separated from the implant. Thus, the successive vibrations from the inserter result in an unseating of the inserter from upon the implant. Once the inserter becomes separated from the implant, the inserter no longer efficiently transfers forces from the mallet blows to the implant. Instead, the mallet blows may result in undesirable forces being applied to the inserter or between the inserter and the implant which adversely effect the integrity of the inserter, the implant, or the surgical procedure.

For example, retraction of the rod from within the implant may damage the rod itself. If the inserter is not seated upon the implant, then some of the forces from the mallet blows are diverted to the rod. The rod, however, is designed to impart compression between the inserter and the implant and is generally not designed to receive impact loads and transfer these impact loads to the implant. Because the rod is not designed to withstand these loads, the impact forces cause damage to the threads, such as by galling, stripping, or flattening the threads. This damage to the threads of the rod may prevent the rod from being completely retracted from the implant, in which case the implant must be removed and replaced with another implant. In addition to damaging the threads, the mallet blows delivered to the inserter may present a sufficiently large enough stress to fracture the rod.

The inserter and implant may also become damaged if the rod retracts from within the implant. For example, as the rod retracts, the load transfer surface on the inserter can become spaced from the implant. This spacing may prevent the load transfer surface of the inserter from being properly aligned with the load transfer surface on the implant. The offset in load transfer surfaces can cause unequal loading within the surfaces resulting in stressing, chipping, or deformation of these surfaces. Because of a spacing between the implant and inserter, the impact forces may also place the inserter in motion relative to the implant and create a collision between the two members. The motion imparted to the inserter aggravates the potential for damage to the inserter or implant.

Besides causing damage to the implant and inserter, a retraction of the rod from within the implant during the impaction process complicates the surgical procedure. If any damage occurs to the rod, other parts of the inserter, or to the implant, the insertion of the implant must be halted and the surgeon must investigate the extent of the damage. The possibility exists that the implant must be removed and the surgeon must repeat certain steps of the procedure. At the very least, damage to the rod, inserter frame, or implant presents a delay which increases the time required within the operating room and necessarily the costs involved in the surgery.

More importantly, damage to the rod, inserter frame, or implant is another complication in the procedure and risk to the patient. For instance, if the rod breaks during the insertion of the implant, the implant having the broken-off portion of the rod must be removed. A retracting mechanism that is typically used to remove the implant, however, also has a rod for insertion within the bore of the implant. The retracting mechanism therefore cannot be readily used to remove the implant. The implant consequently cannot be easily removed from the patient.

The mallet blows directed to the inserter can quickly and unknowingly cause damage without any warning. The retraction of the rod from within the implant during impaction does not follow a linear pattern. Instead, a loosening of the rod promotes additional loosening and compounds upon itself quickly escalating toward possible, probable, or enhanced probability of failure of a component. Thus, even though a surgeon may have fairly recently tightened the inserter to the implant, the rod can retract after only a few blows with the mallet thus causing damage.

It is therefore imperative that forces delivered to an inserter are efficiently delivered to the implant and are not diverted or otherwise transferred to the rod itself. A proposed procedure for ensuring proper seating of the inserter on the implant involves periodically tightening the rod within the implant. A goal of the procedure is to tighten the rod before it becomes too loose with the hopes of preventing any damage from occurring. The proposed procedure involves tightening the rod after every certain set of blows with a mallet, such as after four or five blows.

The proposed procedure in which the surgeon stops and periodically adjusts the inserter is not optimal. For one, retraction of the rod from within the implant is often unpredictable whereby selecting one number may be useful, but may not prevent all damage to the rod, implant, or inserter. Further, the procedure interferes with the surgeon's ability to quickly place the implant at the desired location. Most surgeons prefer to focus on the insertion of the implant and having to stop and tighten the inserter after every four or five blows is a burdensome distraction. A need therefore exists for an inserter that reduces the possibility of damage to the rod, inserter frame, or implant and is better able to remain seated firmly on the implant.

SUMMARY OF THE INVENTION

The present invention addresses the problems described above by providing methods, instruments, and devices for moving objects such as prosthetic implants or instruments to a desired position. An insertion device according to a preferred embodiment of the invention includes an engagement member, such as a rod, that is inserted into an object. The engagement member is contained within a member for transferring forces to the object, such as a frame, that has a load transfer surface, such as feet, for engaging and resting upon the object. In general, a pre-load compression is applied between the inserter and the object to ensure proper seating of the inserter upon the object. This compression ensures that impact forces are transferred to the object and are not diverted to the engagement member or to other portions of the inserter.

In the preferred embodiment, the inserter includes a threaded rod which is inserted into the implant or instrument and a tension is applied to the rod. According to one aspect of the invention, the inserter has a lever which, when closed, results in a resultant force between the rod and a frame of the inserter. This resultant force directs the inserter frame onto the implant to firmly seat the inserter on the implant. The lever has a cammed surface which moves a slider along a length of the rod when the lever is closed. At least one biasing member is positioned between the slider and a thumbscrew which is engaged to the rod. When the lever is closed, the slider is moved closer to the thumbscrew and the biasing member becomes compressed. The biasing member, in turn, opposes these compressive forces, resulting in forces directing the frame of the inserter toward the implant. The biasing member preferably comprises spring washers but may comprise any component, device, or system that applies compression between the inserter and the implant as impact forces are applied to the inserter.

Because compression is applied at all times between the inserter and the implant and tension is applied to the rod, the rod is substantially prevented from becoming loose, thereby minimizing any retraction of the rod from within the implant. Further, even if the rod does retract, the inserter nonetheless remains seated on the implant as long as the distance that the rod retracts remains within the range of the biasing member compression distance. The compression that is applied between the inserter and implant reduces the risk of damage to the rod, other parts of the inserter, or to the implant and thus reduces complications and costs associated with the surgery. On the other hand, inserters without the biasing members have been known to unlock during use.

Accordingly, it is a feature of the present invention to provide methods, systems, and instruments-that efficiently transfer forces to objects such as prosthetic implants or instruments.

It is another feature of the present invention to provide methods, systems, and instruments that are firmly seated on the prosthetic implant or instrument.

It is a further feature of the present invention to provide methods, systems, and instruments that reduce damage to the inserters, the implants, or other instruments.

It is still a further feature of the present invention to provide methods, systems, and instruments that are easily operated.

It is yet another feature of the present invention to provide methods, systems, and instruments for use in positioning implants or instruments at desired locations.

It is still another feature of the present invention to provide methods, systems, and instruments for focusing forces to the implants or instruments.

It is another feature of the present invention to provide methods, systems, and instruments having threaded rods that do not easily become inadvertently unthreaded during use.

It is another feature of the present invention to provide methods, systems, and instruments that do not easily become unseated.

Other objects, features, and advantages of the present invention will become apparent with respect to the remainder of this document.

BRIEF DESCRIPTION OF THE DRAWINGS

The accompanying drawings, which are incorporated in and form a part of the specification, illustrate preferred embodiments of the present invention and, together with the description, disclose the principles of the invention. In the drawings.

DETAILED DESCRIPTION

Figure 1:
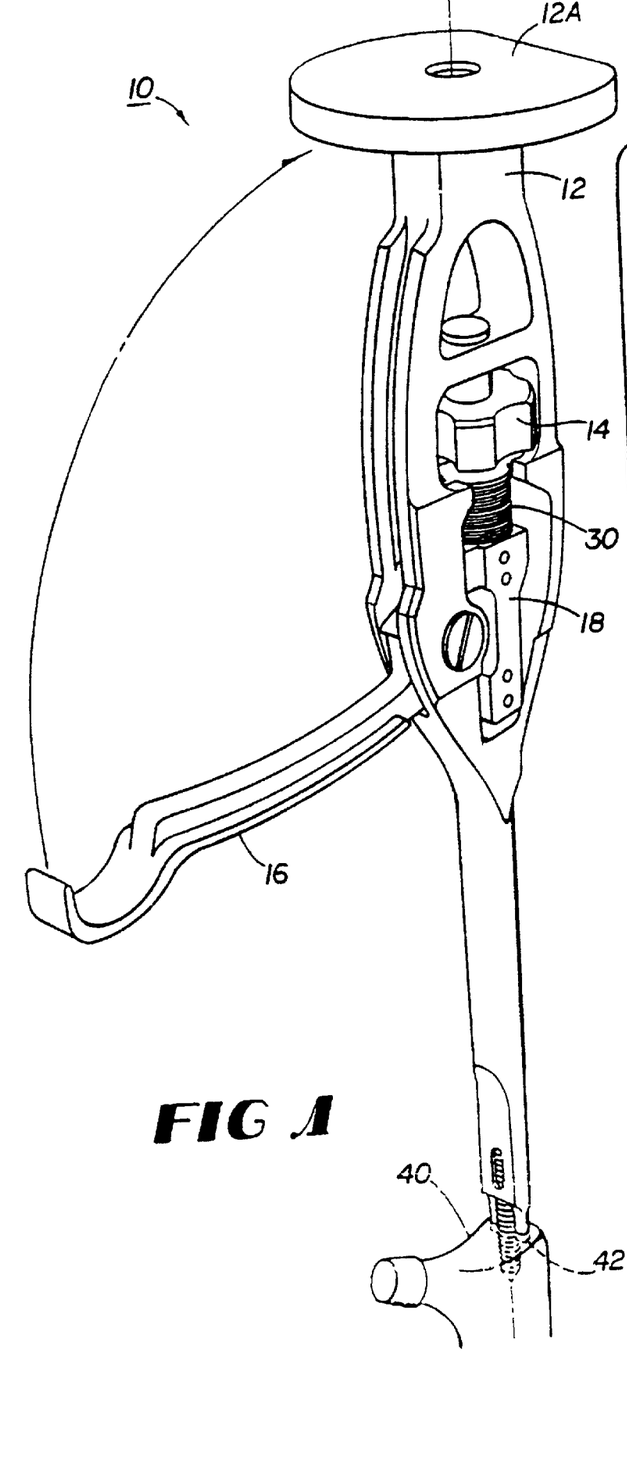
FIG. 1 is a perspective view of an inserter according to a preferred embodiment of the invention.

Reference will now be made in detail to preferred embodiments of the invention, non-limiting examples of which are illustrated in the accompanying drawings. An inserter 10 according to a preferred embodiment of the invention, which is shown in FIG. 1, will now be described with reference to a femoral implant 40 which is to be inserted into the medullary canal of the femur. In general, the inserter 10 according to a preferred embodiment of the invention includes a frame 12 having a surface 12A for receiving forces from an external source and a load transfer surface, which preferably comprises members 12D, for transferring these forces to another object, such as an implant 40. The forces may be received from mallet blows applied to the surface 12A and the inserter 10 passes these forces through its frame 12 to the members 12D. The members 12D are preferably feet that focus the forces upon the implant 40.

The inserter 10 may be attached to the object through any suitable interface between the object and the inserter 10. In the preferred embodiment in which the object to be inserted is the implant 40, the inserter 10 is attached to the implant 40 by turning a thumbscrew 14 so as to thread a rod 24 into the implant 40. After the rod 24 has been hand-tightened into the implant 40, a lever 16 is raised which, as will be described in greater detail below, produces a resultant force that directs the frame 12 of the inserter 10 toward the implant 40. This resultant force works to ensure that the inserter 10 does not become loose during use but instead ensures that the feet 12D are firmly seated on the implant 40. The resultant force generated by the inserter 10 consequently works to prevent any damage either to the rod 24, the frame 12, the implant 40, or other instruments that are being inserted. Furthermore, because of this resultant force, the surgeon does not need to periodically adjust the inserter 10 but rather can focus on inserting the implant 40 to the desired location.

FIG. 1 illustrates just one example of an interface between the frame 12 of the inserter 10 and the implant 40. As shown in more detail in FIG. 2(A), the implant 40 includes a slot recess 42 for receiving the feet 12D of the frame 12. The rod 24 includes a threaded end 24D having a tip 24E which is inserted into a threaded recess 44 of the implant 40; In the interface shown in FIG. 2(A), the driving forces applied and transferred through the frame 12 of the inserter 10 from mallet blows are focused on the feet 12D and are transferred at these points to the implant 40. With this arrangement, the driving forces are isolated from the threaded end 24D of the rod 24 as well as from the threaded recess 44 of the implant 40.

Figure 2A:
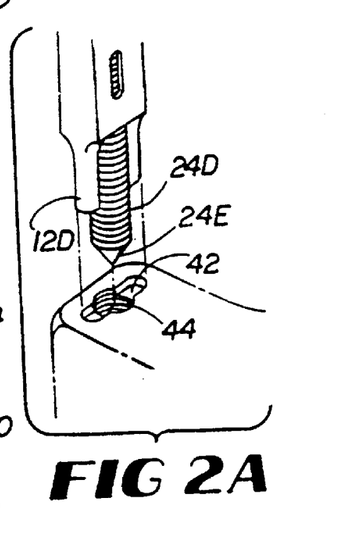
FIG. 2(A) is a partial view of the inserter of FIG. 1 at an interface with an implant having a slot recess.
Figure 2B:
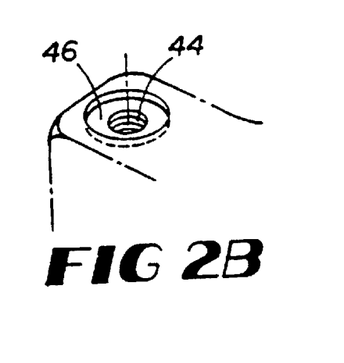
FIG. 2(B) is a perspective view of an interface of an implant according to a second embodiment of the invention having a round recess.
Figure 2C:
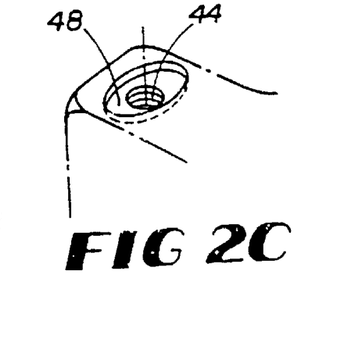
FIG. 2(C) is a perspective view of an interface according to a third embodiment of the invention having an oval recess.

The interface shown in FIGS. 1 and 2(A) is just one example of a suitable interface. As another example, the interface may include a round recess 46 formed on the implant 40 and feet having corresponding rounded end portions. As a further example, the implant 40 may have an oval recess 48, as shown in FIG. 2(C), and the feet may have a corresponding oval shape for being placed within the recess 48. The oval shape shown in FIG. 2(C), as well as other non-circular shapes, are preferably over the circular shape since the inserter may need to be twisted during use and the oval shape prevents rotation of the inserter relative to the implant. The examples of the recesses shown in FIGS. 2(A) to 2(C) have walls which are generally perpendicular to a recessed surface. Alternatively, the walls may be formed at other angles and this recessed surface may be irregularly shaped. For example, with reference to FIG. 2(A), the recess 42 may be V-shaped and the feet 12D may have a corresponding V-shape. Furthermore, instead of a threaded rod and threaded recess within the implant, the inserter may be coupled to the implant or other instrument through other known interfaces or later developed interfaces.

Figure 3:
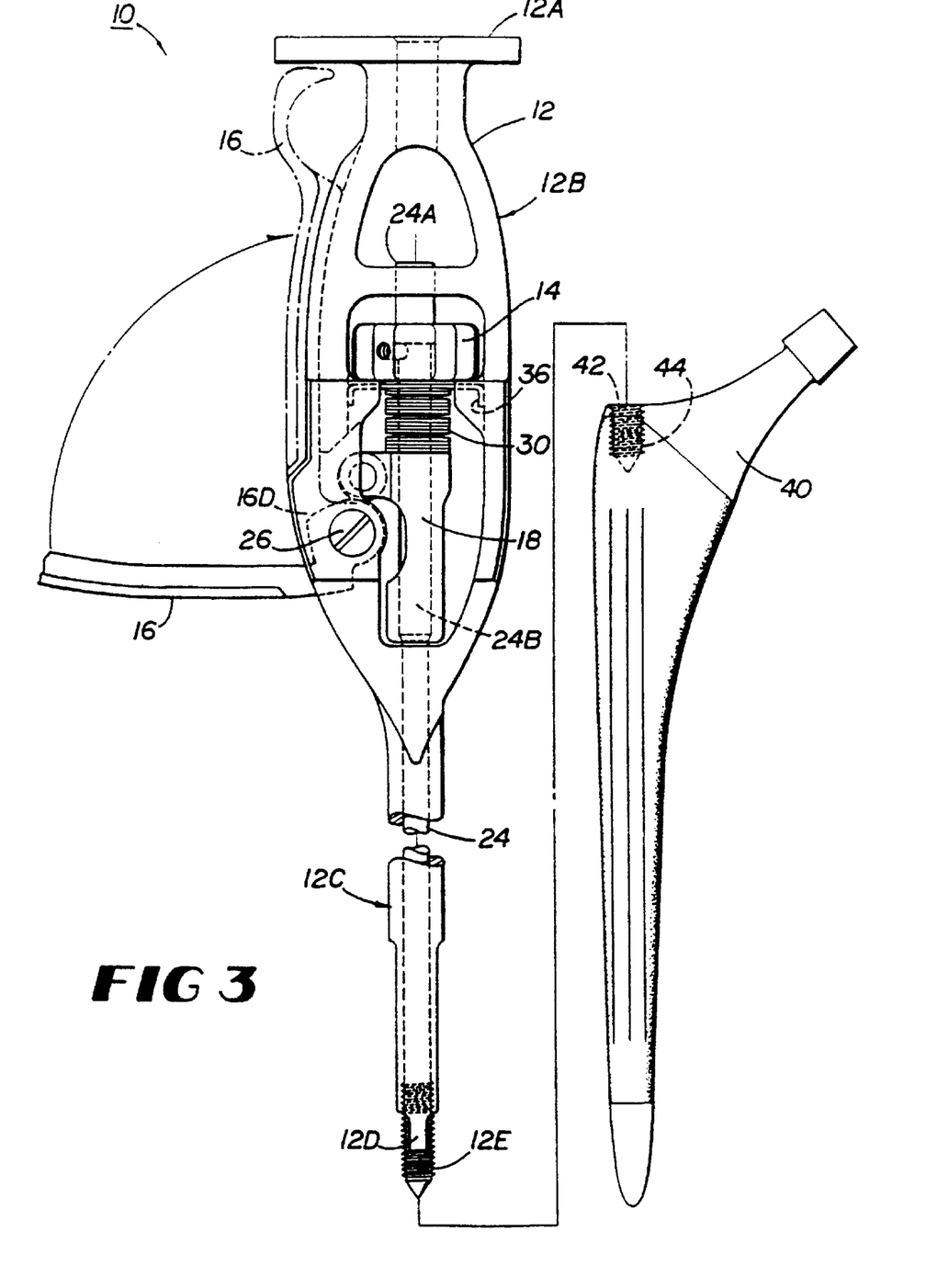
FIG. 3 is a plan view of the inserter of FIG. 1 and its relationship to a femoral implant.

A manner of generating the resultant force that directs the feet 12D of the inserter 10 toward the implant 40 will now be described with reference to FIG. 3. The inserter 10 includes a lever 16, a slider 18, and at least one biasing member 30. The lever 16 has a cammed surface 16D that moves the slider 18 toward the thumbscrew 14 when the lever 16 is pivoted from an open position to a closed position. The at least one biasing member 30 receives compressive forces from being positioned between the moving slider 18 and the thumbscrew 14 which opposes movement of the slider 18. The opposing forces include one component which is applied to the thumbscrew 14 in a direction away from the implant 40 and a second component that is applied to the slider 18 and frame 12 in a direction toward the implant 40. The resultant force is therefore one that firmly seats the feet 12D of the frame 12 on the implant.

In the preferred embodiment, the biasing member 30 comprises a set of spring washers, such as Belleville spring washers manufactured by Lee Spring Company of Brooklyn, New York. The Belleville spring washers 30 are able to provide high loads in restricted spaces and a desired load can be calculated according to the configuration of the washers. For example, washers which are all oriented in the same direction are considered to be in parallel whereas washers which are arranged in opposite configurations are considered to be in series. For example, in the preferred embodiment the Belleville spring washer comprises Part No. 312-030-625, has a thickness of 0.030 inches, and requires a load of 178 lbs. to flatten the washer. Using the spring constant of the washers 30, those skilled in the art can place the washers 30 in parallel or series to derive a desired force when the washers 30 are compressed a desired distance. This desired distance is the distance that the slider 18 travels toward the thumbscrew 14 after the spring engagement upon closing of the lever 16. The resultant force should be selected to be large enough to ensure proper seating of the feet 12D upon the implant 40, be small enough to not cause damage to the threads of the rod 24 and small enough to allow the lever 16 to completely close with a force that can be delivered with average or typical human strength. In this example, the resultant force is 320 lbs. and the distance that the slider 18 travels while compressing the spring washers 30 is 0.065 inches.

Figure 4:
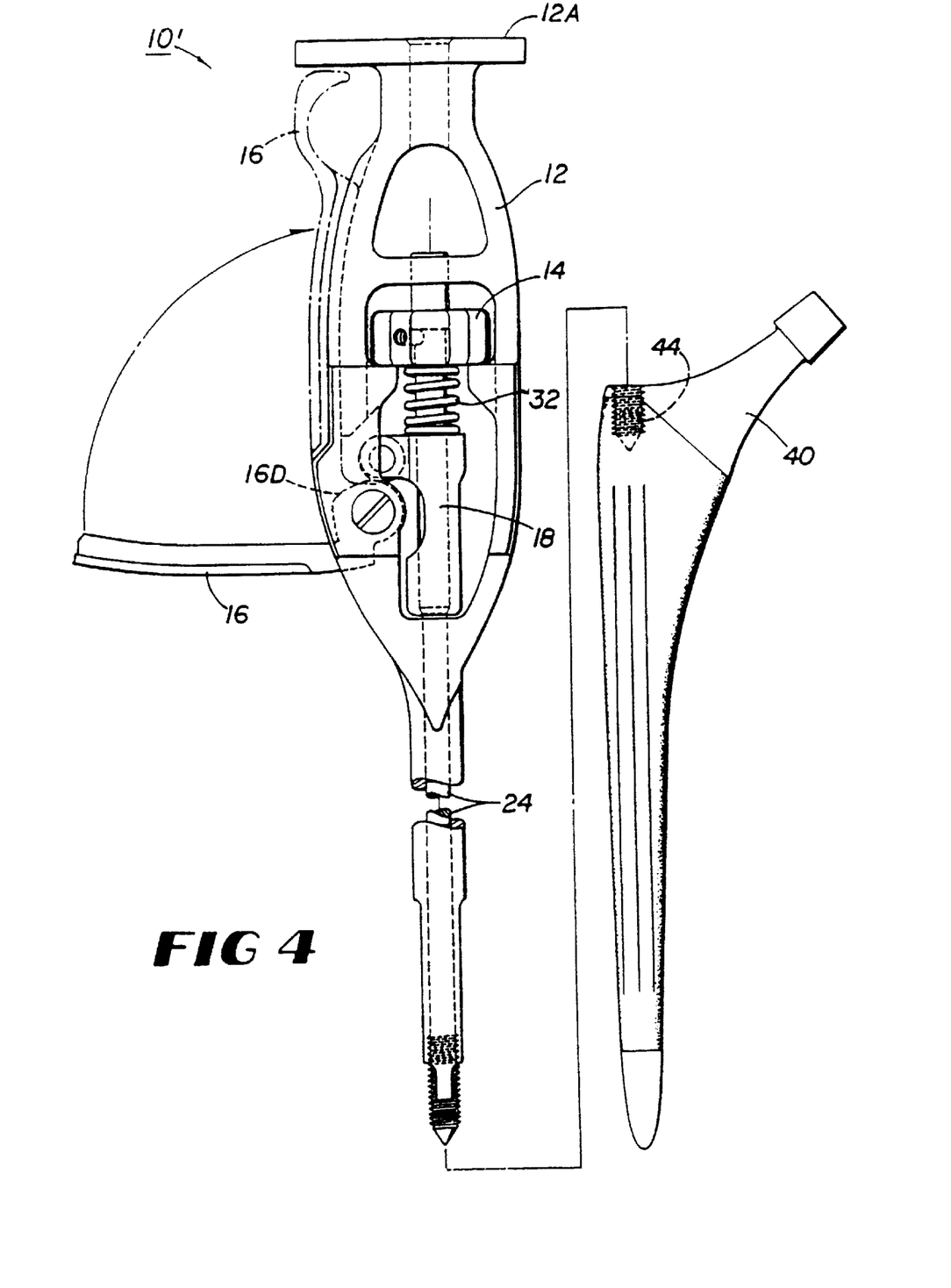
FIG. 4 is a side view of an inserter according to a second embodiment of the invention and its relationship to a femoral implant.

The biasing member 30 is not limited to a spring washer but may be replaced with other elements. As one example, as shown in FIG. 4, an inserter 10' may include a compression spring 32 positioned between the slider 18 and the thumbscrew 14. By closing the lever 16, the spring 32 becomes compressed and generates forces that cause the frame 12 of the inserter 10' to remain compressed against the implant 40. Also, leaf springs or wave springs may be used to provide compression between the frame 12 and implant 40. Furthermore, a torsion spring could also be used or a solid material, such as rubber or elastic plastic, could be used to provide forces to the rod 24 and frame 12 to ensure compression between the inserter and implant or other instrument. As a further example, the biasing member may be integral with the rod 24 itself or with the slider 18 itself. The rod may be formed of an elastic material or may include an elastic member that provides additional tension to the rod. The slider may also be made such that it provides a biasing action in a similar manner as the rod.

Figure 5:
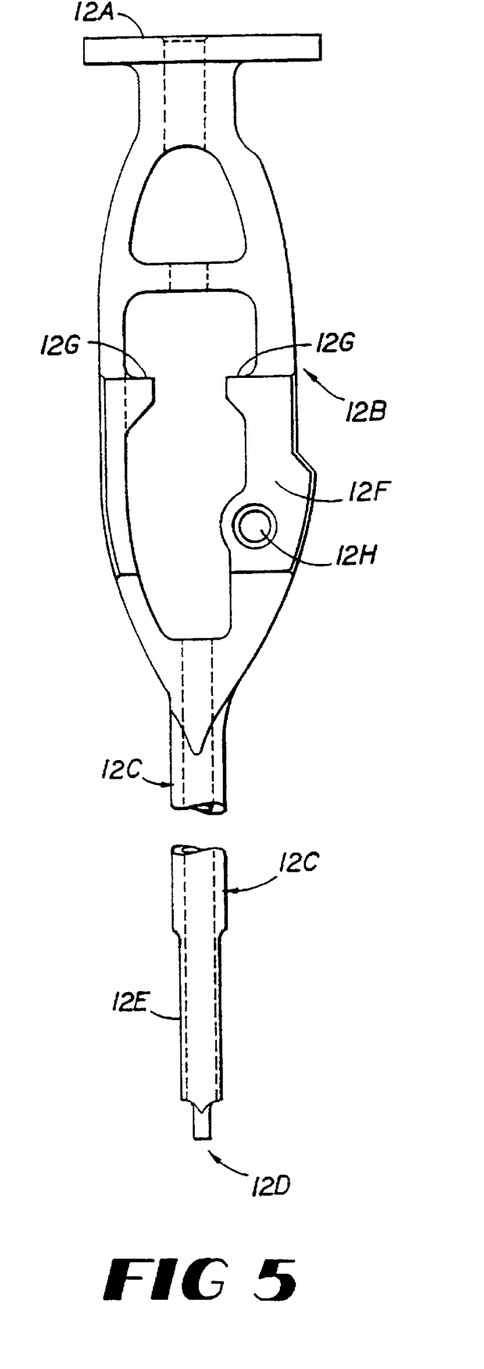
FIG. 5 is a side view of a stem inserter frame according to a preferred embodiment of the invention.

With reference to FIG. 5, the frame 12 of the inserter 10 has a surface 12A that is sized and shaped to receive forces from an external source, such as blows from a mallet. The forces applied to the surface 12A are transferred from surface 12A, through a section 12B, along section 12C, to the feet 12D. The frame 12 includes a central aperture 12E within which the rod 24 is received. The feet 12D are placed on either side of the aperture 12E to evenly distribute forces to the implant 40. Section 12B may be grasped by a surgeon and includes a channel 12F, ledges 12G, and apertures 12H. The ledges 12G protrude inwardly from sides of the frame 12 and, as better shown in FIGS. 1, 3, and 4, limit movement of the thumbscrew 14 toward the feet 12D of the frame 12.

Figure 6:
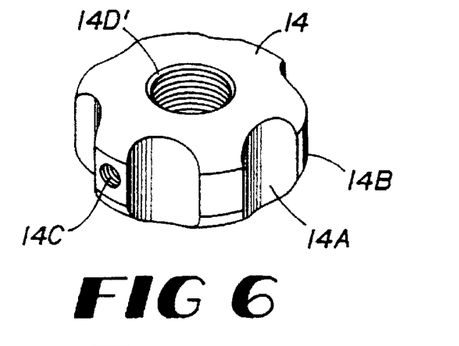
FIG. 6 is a perspective view of stem inserter thumbscrew according to a preferred embodiment of the invention.

A preferred embodiment of the thumbscrew 14 is shown in FIG. 6. The thumbscrew 14 has recessed portions 14A, raised portions 14B, and a central aperture 14D which is sized and shaped to receive an upper section of the rod 24. The aperture 14D includes a portion with a reduced diameter which prevents an enlarged section 24A of the rod 24 from traveling toward the implant 40. Thus, the thumbscrew 14 is unable to travel upwardly along the length of the rod 24 and, as discussed above, is also unable to travel downwardly toward the feet 12D due to ledges 12G. The thumbscrew 14 also includes an aperture 14C for receiving a pin, such as a press fit pin, which secures thumbscrew 14 to rod 24. The press fit pin secures the thumbscrew 14 so that the rod 24 rotates upon rotation of the thumbscrew 14. In an alternative embodiment, thumbscrew 14 includes a threaded aperture for receiving a set screw, which secures thumbscrew 14 to rod 24. The set screw secures the thumbscrew 14 so that the rod 24 rotates upon rotation of the thumbscrew 14.

Figure 7:
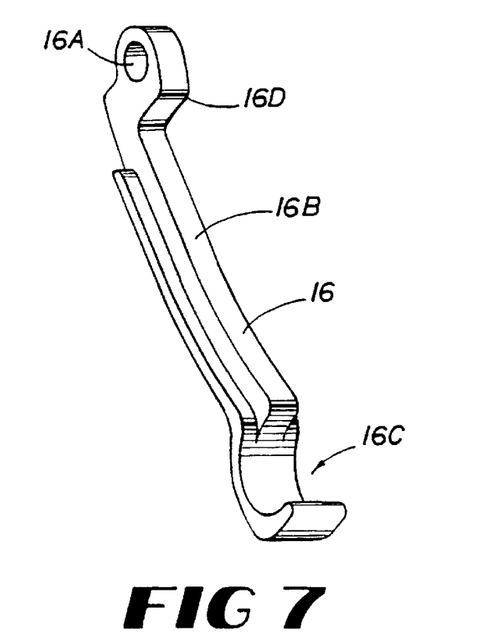
FIG. 7 is a perspective view of a stem inserter lever according to a preferred embodiment of the invention.

A preferred embodiment of the lever 16 is shown in FIG. 7. The lever 16 includes an aperture 16A about which the lever 16 pivots. The lever 16 terminates in a curved portion 16C which, as shown in FIG. 3, provides a space between the lever 16 and the frame 12 of the inserter 10. This space is preferably large enough to allow a user to insert a finger into this aperture to apply forces to lower the lever 16 and pivot it away from the frame 12. The lever 16 also includes a ribbed portion 16B for being received within a corresponding slot within the frame 12. The lever 16 also includes a cammed portion 16D for moving the slider 18 toward the thumbscrew 14 when then lever 16 is pivoted toward the frame 12.

The cammed portion 16D of the lever 16 is shaped so that the lever 16 is over-centered and is biased closed when placed against the frame 12. The lever 16 should not inadvertently become lowered and opened during the delivery of mallet blows to the frame 12 since the lever 16 must be forced beyond the apex of the cammed surface 16D in order to lower the lever 16. While closing the lever 16, a maximum clamping force is applied to the spring washers 30 when the apex of the cammed surface 16D contacts the roller 20. When the lever 16 is moved to a completely closed position, the clamping force applied to the spring washers 30 drops to a level below that maximum clamping force. The spring washers 30 or other types of biasing members advantageously provide tension to the rod 24 and compression between the inserter 10 and implant 40 even after the compressive forces applied to the biasing members 30 drop below this maximum clamping force.

Figure 8:
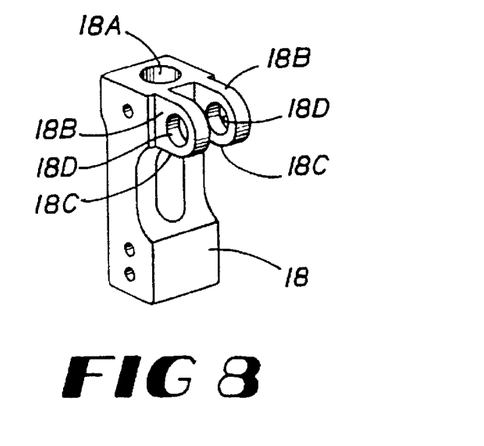
FIG. 8 is a perspective view of a stem inserter slider according to a preferred embodiment of the invention.
Figure 9:
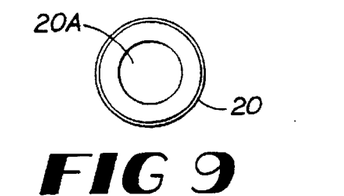
FIG. 9 is a plan view of a stem inserter roller according to a preferred embodiment of the invention.
Figure 10:
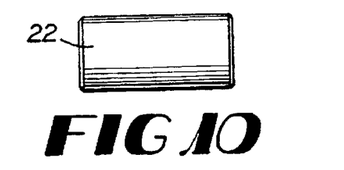
FIG. 10 is a plan view of a stem inserter roller pin according to a preferred embodiment of the invention.

A preferred embodiment of the slider 18 is shown in FIG. 8. The slider 18 has an aperture 18A through which the rod 24 passes. The slider 18 also includes members 18B that have apertures 18D. A roller 20, as shown in FIG. 9, is inserted between the two members 18B and provides a relatively low friction interface between the slider 18 and the lever 16. The roller 20 has a central aperture 20A through which a roller pin 22 passes. The roller pin 22 is shown in more detail in FIG. 10 and, in addition to being inserted into the roller 20, is also inserted through the apertures 18D of the slider 18. The roller pin 22 is contained within the apertures 18D of members 18B and consequently maintains the roller 20 within the members 18B as well. The roller pin 22 travels within the channel 12F within the frame 12.

Figure 11:
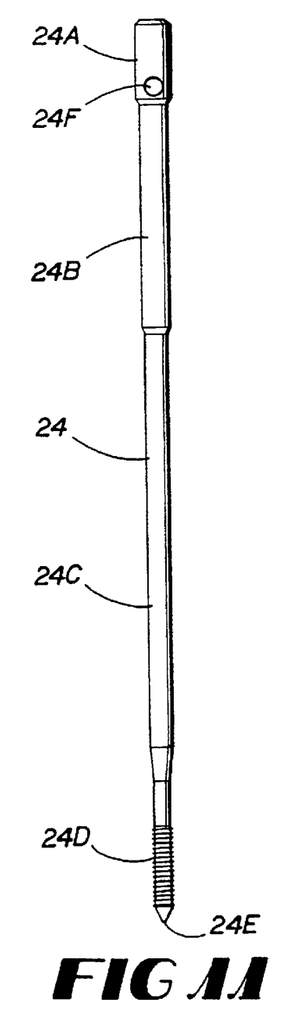
FIG. 11 is a side view of a stem inserter rod according to a preferred embodiment of the invention.

A preferred embodiment of the rod 24 is shown in FIG. 11. The rod 24 includes section 24A which has an enlarged diameter relative to portion 24B. As discussed above, the section 24A of the rod 24 is inserted within the thumbscrew 14 but is unable to pass completely through the thumbscrew 14 due to the shape of the central aperture 14D within the thumbscrew 14. The rod 24 also includes a section 24B which, as shown in FIG. 3 and 4, is partially contained within the slider 18 and a section 24C which runs through section 12C of the frame 12. The threaded end 24D of the rod 24 has the tip 24E for being inserted into the implant 40. Aperture 24F is adapted to receive a press fit pin to secure the thumbscrew 14 to the rod 24.

Figure 12:
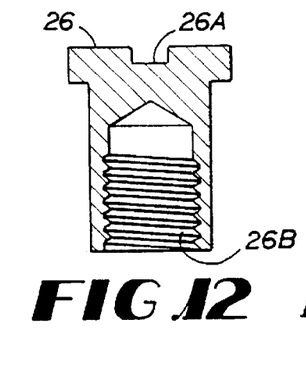
FIG. 12 is a side view of a stem inserter female pin according to a preferred embodiment of the invention.
Figure 13:
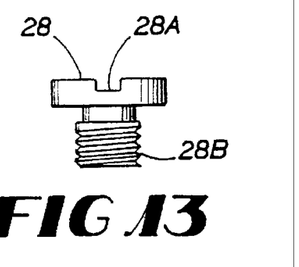
FIG. 13 is a side view of a stem inserter male pin according to a preferred embodiment of the invention.

A preferred embodiment of a pin for securing the lever 16 to the frame 12 is shown in FIGS. 12 and 13. The pin in this example is comprised of a female pin 26 and a corresponding male pin 28 with the female pin 26 having a threaded section 26B for receiving threads 28B on the male pin 28. Both the female pin 26 and the male pin 28 have slots 26A and 28A, respectively, for receiving the end of a screw driver. The female pin 26 is passed through apertures 12H in the frame 12 and through aperture 16A in the lever 16 and the male pin 28 is passed through the other aperture 12H of the frame 12 and into the female pin 26. The pins 26 and 28, of course, are just one example of a way that the lever 16 may be secured in a pivotal fashion to the frame 12.

Figure 14A:
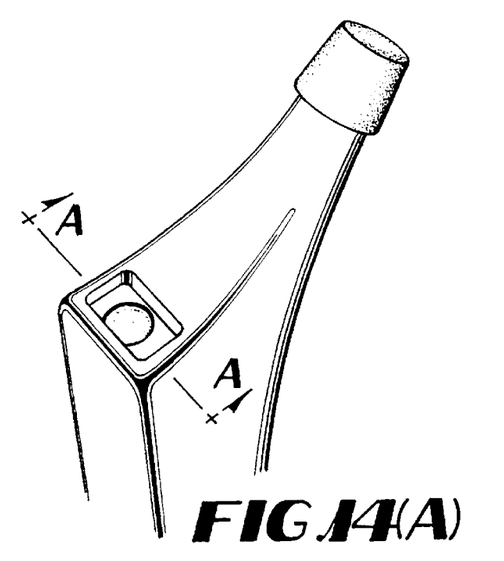
FIG. 14(A) is a perspective view of a captive ball lock interface according to an alternate aspect of the invention.
Figure 14B:
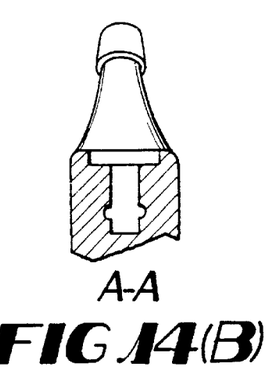
FIG. 14(B) is a partial view in cross section of the interface of FIG. 14(A)
Figure 14C:
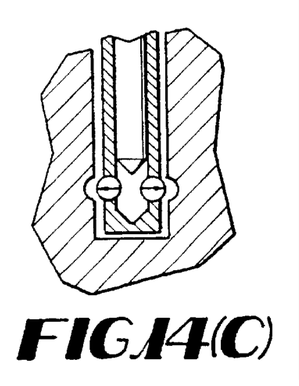
FIG. 14(C) is a partial view in cross section of the interface of FIG. 14(A).
Figure 15:
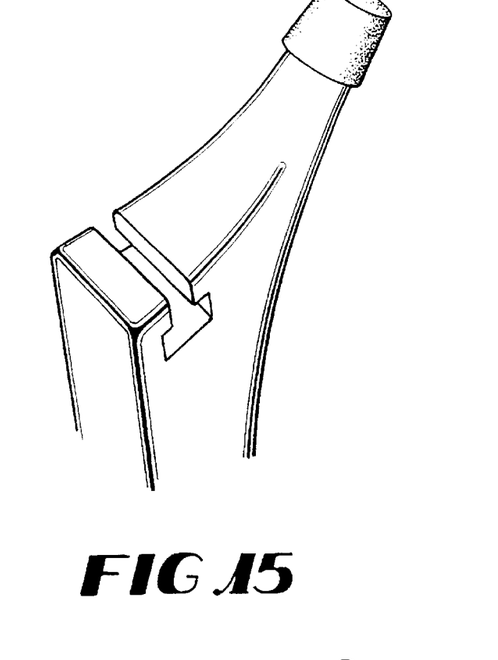
FIG. 15 is a perspective view of a T-slot interface according to an alternate aspect of the invention.
Figure 16A:
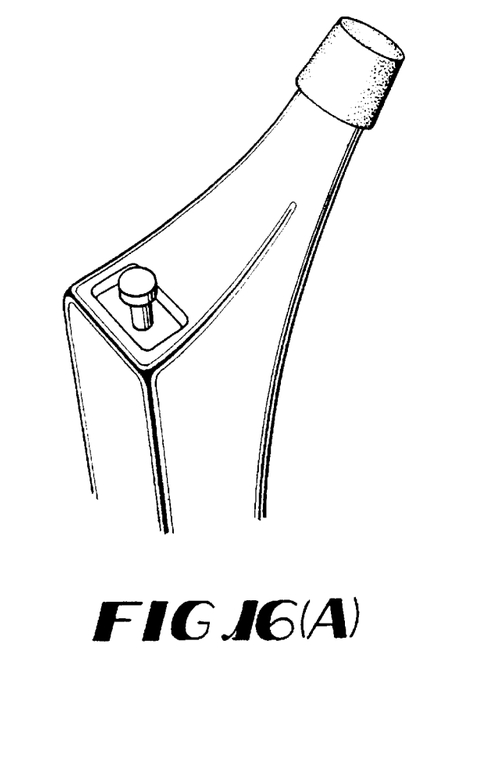
FIG. 16(A) is a perspective view of a contracting collet lock interface according to an alternate aspect of the invention.
Figure 16B:
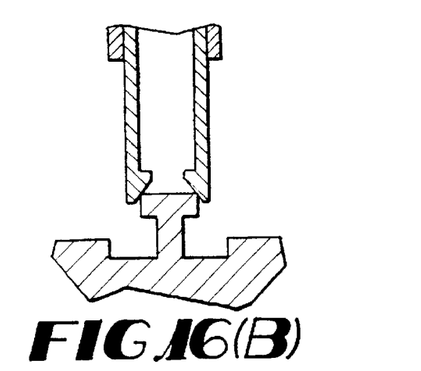
FIGS. 16(B) to 16(E) are partial side views in cross section of the interface of FIG. 16(A), showing the attachment of the contracting collet lock interface to an implant.
Figure 16C:
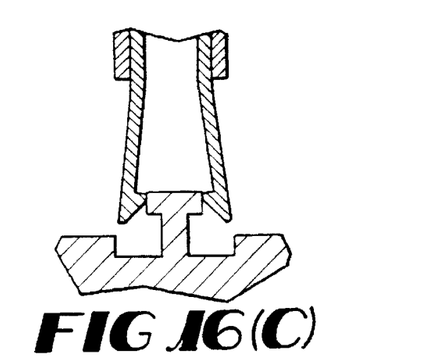
Figure 16D:
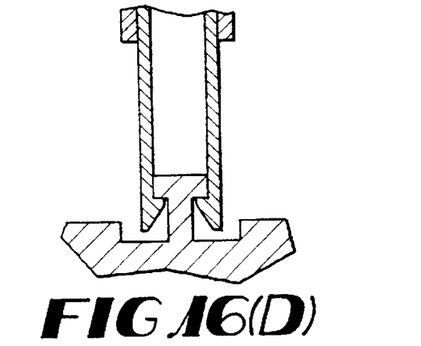
Figure 16E:
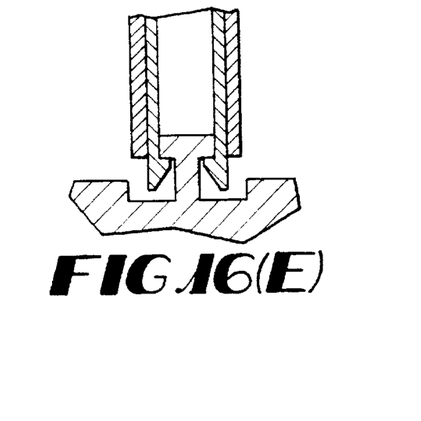
Figure 17:
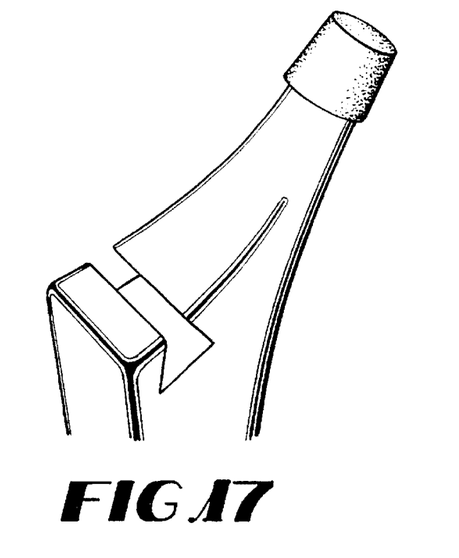
FIG. 17 is a perspective view of a taper slot interface according to an alternate aspect of the invention.

As discussed above, the invention is not limited to any particular interface between the inserter and implant or other instrument. Some non-limiting examples of other possible interfaces are shown in FIGS. 14 to 21. FIGS. 14(A) to 14(C) illustrate a captive ball lock interface which includes members, such as balls, for being pressed into notches upon receipt of the inserter. FIG. 15 depicts a T-slot interface in which the implant or instrument includes a T-slot and the inserter includes a T-shaped member for sliding into the slot. FIGS. 16(A) to (E) illustrate a contracting collet lock in which the inserter includes collet arms and an outer sleeve. When placing the inserter onto the implant, the collet arms pass over a collet on the implant and the outer sleeve moves toward the implant to provide a secure attachment. FIG. 17 depicts an interface in which the implant includes a taper slot and the inserter includes a correspondingly shaped member for being inserted into the slot.

Figure 18A:
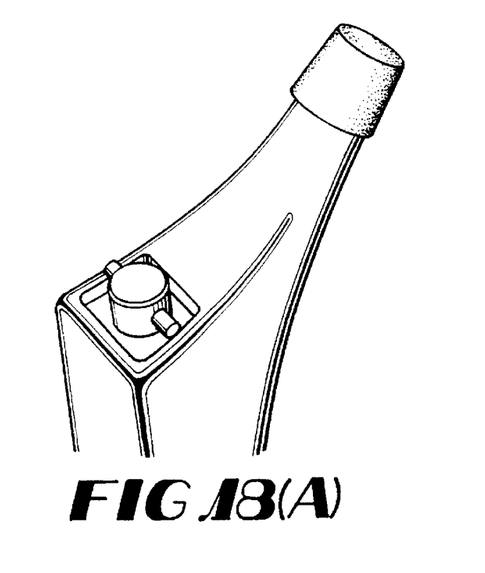
FIG. 18(A) is a perspective view of an interface according to an alternate aspect of the invention which includes a pegs and slot arrangement.
Figure 18B:
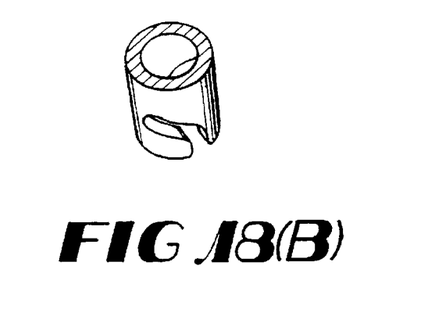
FIG. 18(B) is a perspective view of the post of FIG. 18(A)
Figure 19A:
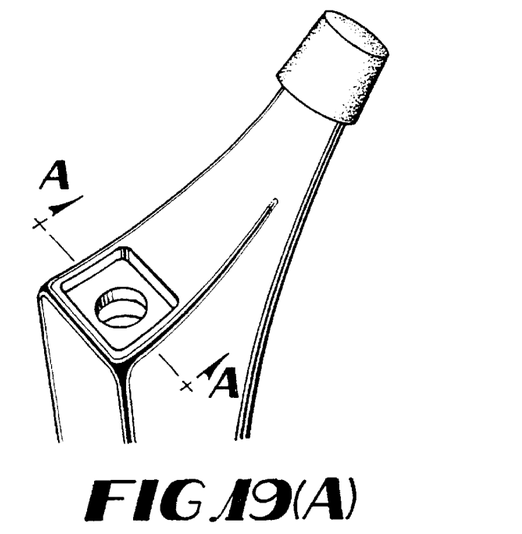
FIGS. 19(A) is a perspective view of an expanding collet lock interface according to an alternate aspect of the invention.
Figure 19B:
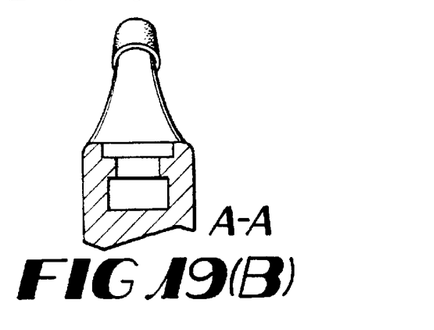
FIGS. 19(B) to 19(D) are partial views in cross section of the interface of FIG. 19(A) showing the attachment of the expanding collet lock interface to an implant.
Figure 19C:
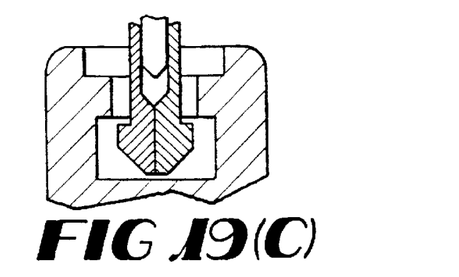
Figure 19D:
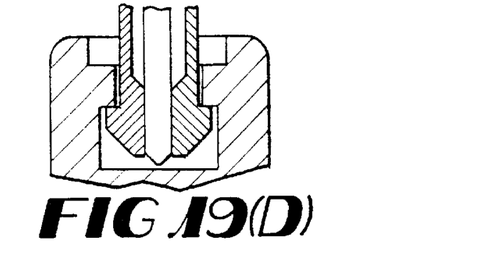

Another variation on the interface is shown in FIGS. 18(A) and (B). FIG. 18(A) illustrates an implant having a post with pegs and FIG. 18(B) shows a fastener on the inserter having slots for receiving the pegs. The inserter is placed onto the implant with the pegs placed into the slots and the inserter is rotated in order to secure the two members together.

An expanding collet lock type of interface is shown in FIGS. 19(A) to (D). The inserter includes collet arms which are placed within a T-shaped recess within the implant. The inserter also includes a center pin which moves toward the implant and forces the collet arms into engagement with the T-shaped recess.

Figure 20A:
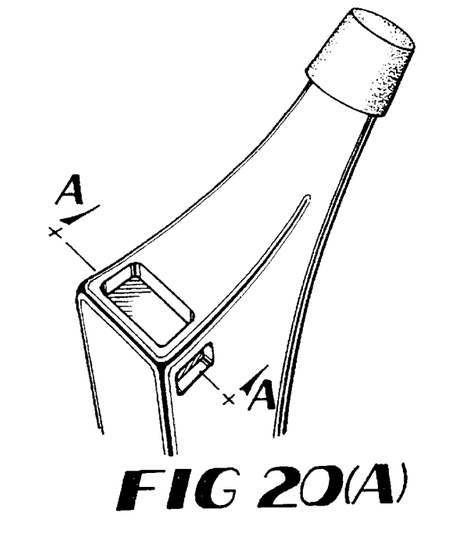
FIG. 20(A) is a perspective view of an interface according to an alternate aspect of the invention that has side slots for receiving collet or hook locks.
Figure 20B:
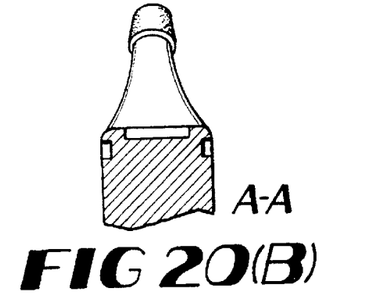
FIG. 20(B) is a partial view in cross section of the interface of FIG. 20(A)
Figure 21A:
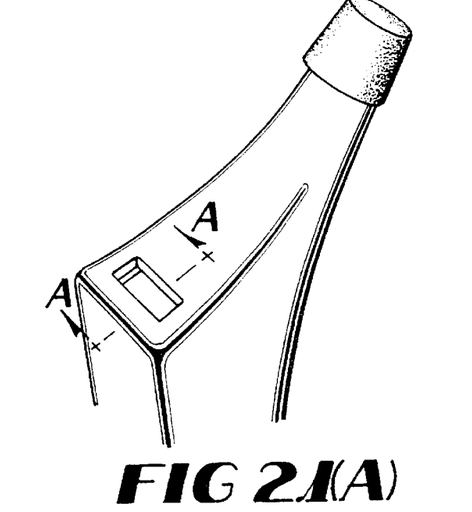
FIG. 21(A) is a perspective view of a key lock interface according to an alternate aspect of the invention.
Figure 21B:
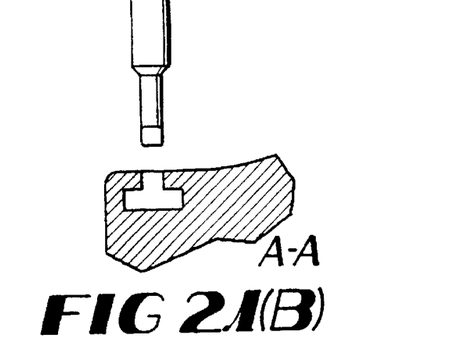
FIGS. 21(B) to 21(D) are partial views in cross section of the interface of FIG. 21(A) showing the attachment of the key lock interface to an implant.
Figure 21C:
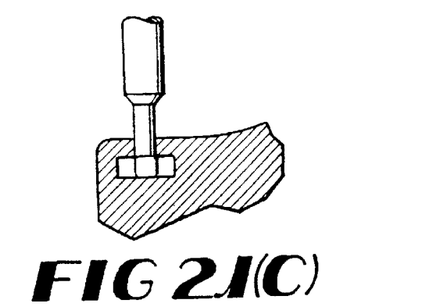
Figure 21D:
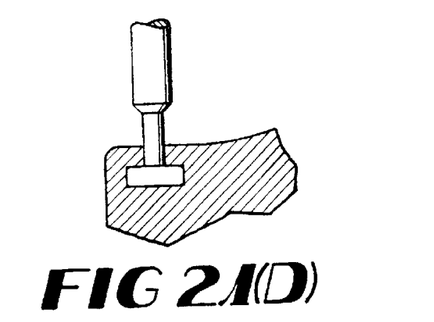
Figure 21E:
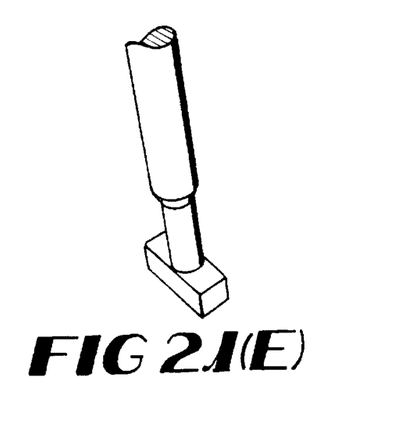
FIG. 21(E) is a perspective view of the key of FIG. 21(A)

Another example of an interface is shown in FIGS. 20(A) and 20(B). This interface includes side slots on the implant as well as a slot on the top surface of the implant. The top slot may comprise any type of interface, such as a threaded recess that receives a threaded rod, and the inserter includes members for locking into the side slots of the implant. These additional members on the inserter may be contracting collets or hook locks.

Yet another example of an interface is shown in FIGS. 21(A) to 21(E). In this example, the inserter includes a key that is inserted into a lock within the implant. As shown in the sequence depicted in FIGS. 21(B) to 21(D), the key is inserted into the lock and then rotated a quarter turn to lock the inserter to the implant.

The invention is not limited to inserters for use with femoral implants but also relates to inserters for inserting other types of prosthetic implants, to prosthetic implants inserted into other bones, and even to devices, members, or structures other than prosthetic implants. For example, other instruments and devices that may be driven to a desired position with the inserter includes broaches, reamers, alignment tools, depth guides, and gauges. Furthermore, while use of the inserters in a preferred application of the inserter results in impacting the medullary canal of a bone, the inserters may be used in applications that do not result in any impacting of a bone. A force may need to be transferred through the inserter and delivered to another object for various reasons other than for forcing the implant to a desired position within a patient.

Figures 22A, 22B:
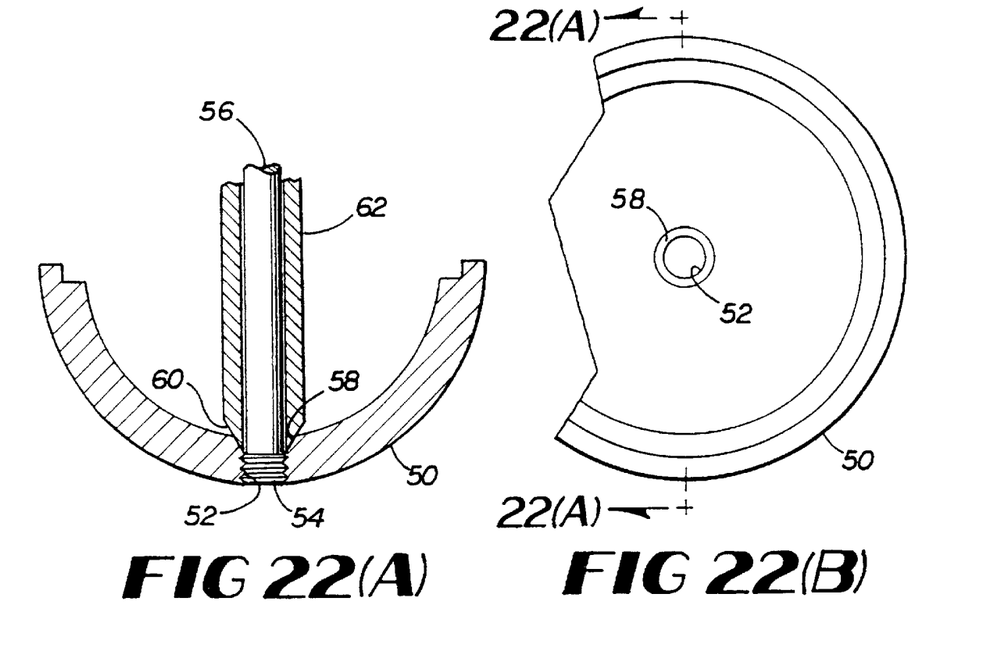
FIG. 22(A) is a side view in cross section of a chamfer friction lock interface with an acetabular shell according to an alternative embodiment of the invention.
FIG. 22(B) is a plan view of the acetabular shell of FIG. 22(A)

In an alternative embodiment of the invention, an inserter is used to insert an acetabular shell. FIG. 22(A) illustrates a chamfer friction lock interface between the inserter and an acetabular shell 50. Acetabular shell 50 includes a threaded aperture 52 through which the threaded end 54 of rod 56 is inserted. The acetabular shell 50 includes chamfer surface 58. Chamfer surface 58 and the end 60 of the frame 62 are formed in complementary shapes so that they join in a mating relationship. FIG. 22(B) is a plan view of the acetabular shell 50. As discussed with reference to the embodiments described above, the inserter also includes a biasing member for forcing the end 60 into contact with the shell 50. Although not shown, the inserter shown in FIG. 22(A) is able to generate a compressive force directing the end 60 toward the shell 50.

Figures 23A, 23B:
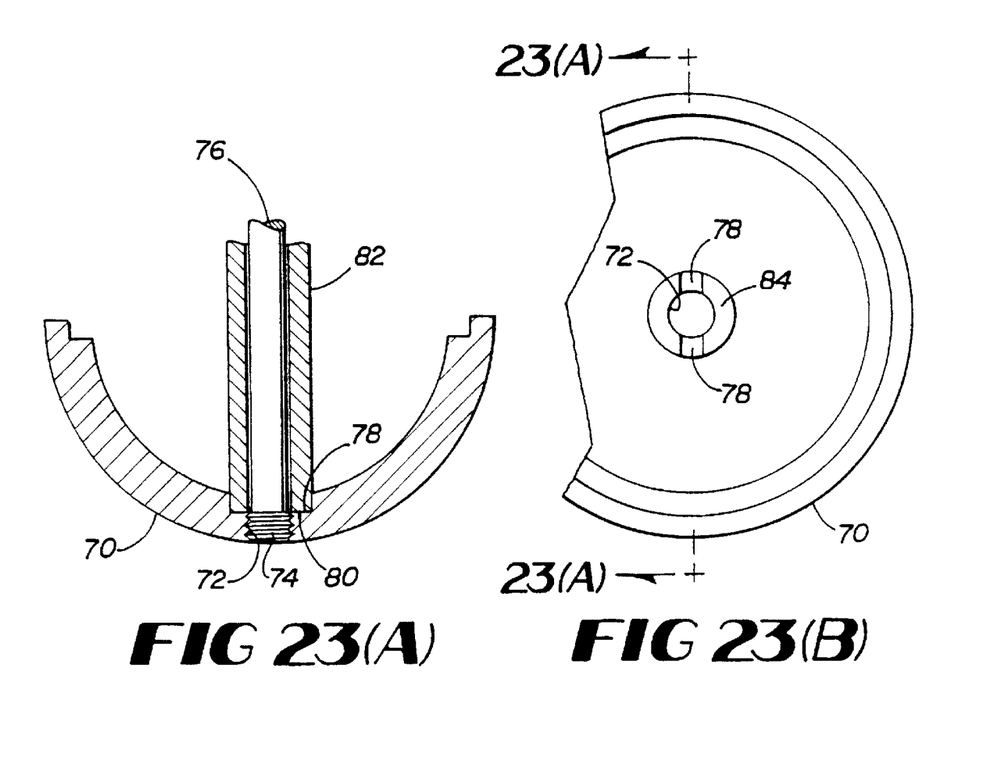
FIG. 23(A) is a side view in cross section of a chamfer shoulder lock interface with an acetabular shell according to an alternative embodiment of the invention.
FIG. 23(B) is a plan view of the acetabular shell of FIG. 23(A)
Figure 23C:
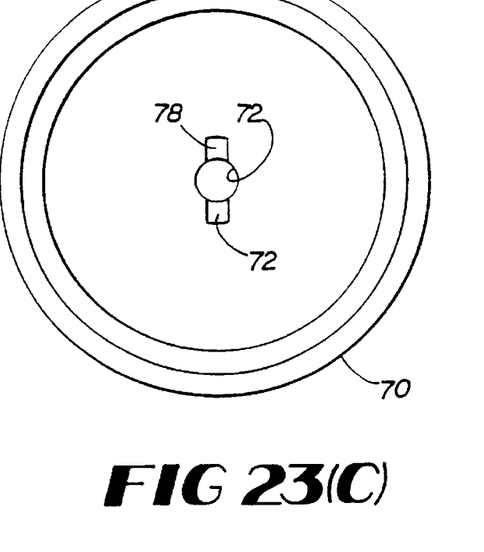
FIG. 23(C) is a plan view of an acetabular shell having a shoulder interface but no chamfer.

FIG. 23(A) depicts a chamfer shoulder lock interface with acetabular cup 70. Similar to the friction lock interface described above, acetabular shell 70 includes threaded aperture 72 for receiving the threaded end 74 of rod 76. Acetabular shell 70 includes shoulders 78 for receiving feet 80 of the frame 82. FIG. 23(B) is a plan view of one embodiment of the acetabular shell of FIG. 23(A) and depicts shoulders 78, aperture 72 and chamfer 84. FIG. 23(C) is a plan view of an alternative embodiment of an acetabular shell having shoulders 78 and aperture 72 but without a chamfer. Although not shown, the inserter shown in FIG. 23(A) is able to generate a compressive force directing the feet 80 toward the shell 70.

The invention has been described with reference to inserters that have at least one biasing member for applying tension to the rod and/or compression between the inserter and the implant or instrument. Although in the embodiments disclosed the biasing members comprise Belleville spring washers or a compression spring, the biasing members should not be limited to these examples. As discussed above, some examples of other members include extension springs, leaf springs, wave springs, torsion springs, rubber members, and elastic plastic members.

Figure 24:
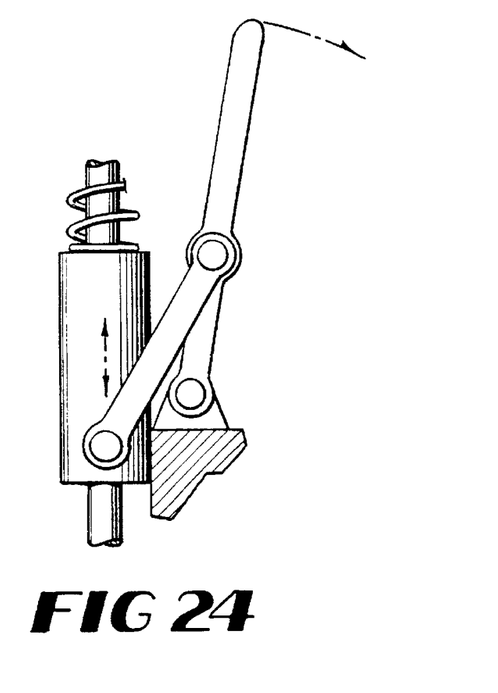
FIG. 24 is a diagrammatic side view of a locking latch arrangement according to an alternative embodiment of the invention.
Figure 25:
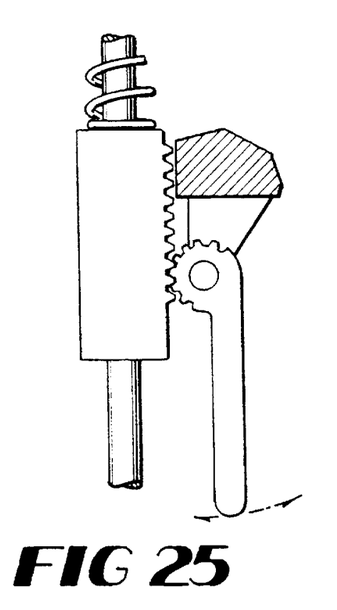
FIG. 25 is a diagrammatic side view of a rack and pinion arrangement according to an alternative embodiment of the invention.
Figure 26:
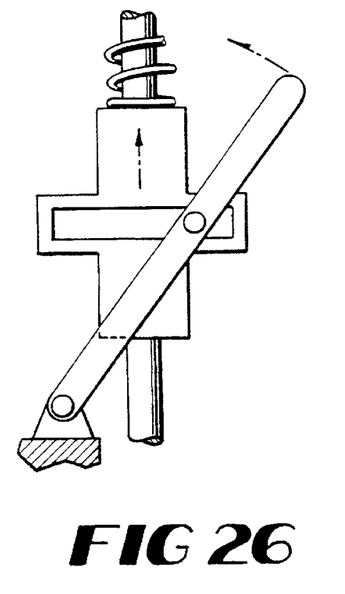
FIG. 26 is a diagrammatic side view of a scotch yoke arrangement according to an alternative embodiment of the invention.
Figure 27:
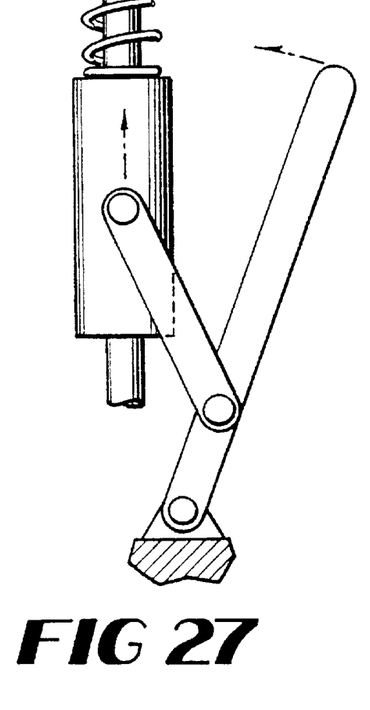
FIG. 27 is a diagrammatic side view of a toggle clamp arrangement according to an alternative embodiment of the invention.

The invention is also not limited to the arrangement of the biasing member, thumbscrew, and slider. For example, as shown in FIG. 24, the compression between the inserter and implant or instrument may be provided through a latch arrangement. By closing the lever, the lever pulls the slider to compress the biasing member, resulting in tension being applied to the rod and compression being provided between the inserter and implant or instrument. As another example, the lever and slider may form a rack and pinion arrangement in which closing of the lever results in compression of the biasing member, as shown in FIG. 25. Also, the lever and slider may form a scotch yoke in which the lever has a pin that slides within a groove in the slider, as shown in FIG. 26. By closing the lever, the pin travels along the groove and moves the slider so that the biasing member becomes compressed. Additionally, as shown in FIG. 27, the lever and slider may form a toggle clamp in which closing of the lever pushes the slider to compress the biasing member.

Other mechanisms, devices, members may be used to impart compression between the inserter and the implant or instrument or tension to the rod.

Figure 28:
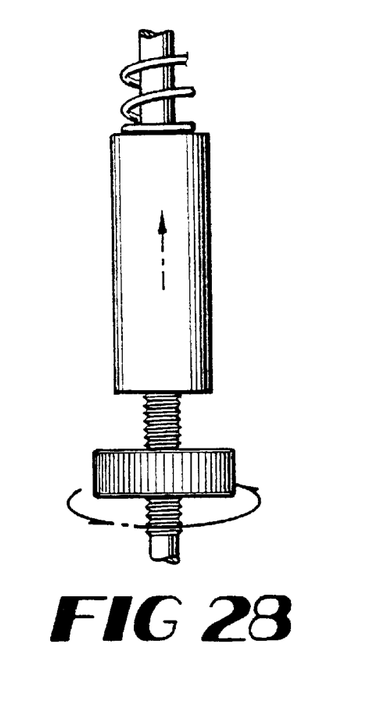
FIG. 28 is a diagrammatic side view of a secondary thumbscrew according to an alternative embodiment of the invention.

The invention is not limited to a lever for causing compression of the biasing member. The examples listed above describe various arrangements that include a lever for causing a slider to compress the biasing member. Instead of a lever, other members or devices may be used to move a slider so that the biasing member becomes compressed. For instance, a secondary thumbscrew may be provided on a side of the slider opposite the biasing member, as shown in FIG. 28. After tension has been applied to the rod through tightening of a main thumbscrew, such as thumbscrew 14, the secondary thumbscrew is rotated so as to move the slider closer to the thumbscrew 14.

Furthermore, the inserters may include additional devices or structures for locking the lever 16 in a desired position. For instance, when the lever 16 is closed and is positioned close to the frame 12 of the inserter, the inserter 10 may include structure or a device for preventing the lever 16 from inadvertently opening. Moreover, while the cam operated lever in combination with the biasing member is the preferred structure used in generating the compression between the inserter and the implant, the invention includes other possible structures or devices that exist which can be used to generate a compression.

Figure 29:
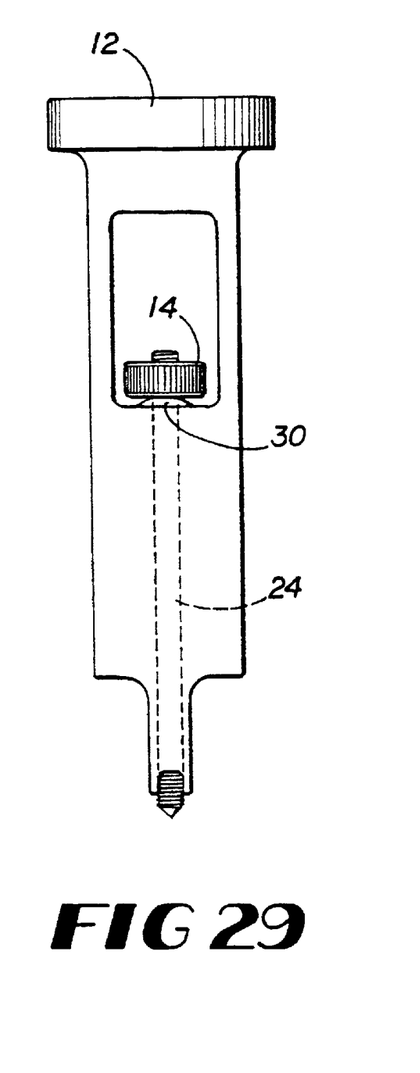
FIG. 29 is a diagrammatic side view of a further embodiment of an inserter which has a biasing member between a thumbscrew and frame of the inserter.

A further embodiment of the invention is shown in FIG. 29. In this example, the biasing member 30, which preferably is the spring washer, is inserted between the thumbscrew 14 and the frame 12 of the inserter. The thumbscrew 14 is rotated until it is completely threaded within the implant or the instrument and then is rotated an additional amount to compress the spring washer 30. The one or more spring washers 30 provide tension to the rod 24 and generate a resultant force which compresses the frame 12 of the inserter upon the implant or instrument.

The invention has been described with reference to the use of one or more biasing members to provide compression between the inserter and the implant or instrument. In the preferred embodiment, the biasing members ensure proper compression even if a rod retracts from within the implant or instrument. It should be understood that the one or more biasing members may ensure proper compression in response to other events. For instance, backlash from actuating gears and looseness in mechanical system due to tolerances or physical deformation can also be compensated for by the one or more biasing members.

The inserters according to the invention have advantages over existing inserters or impactors. For one, a constant compression is applied between the inserters and the implant and this compression reduces any retraction of the rod from within the implant. The compression also ensures that the inserter is properly seated upon the implant, even if the rod begins to unthread. The inserters according to the invention should exhibit less damage to the rod during use as well as less damage to the implants. The compression that is applied between the inserters and the implant direct impact forces to the load transfer surface of the inserter and not to other members, such as the rod. Consequently, the impact forces should not damage the threads or cause any fracture of the rod.

The compression, by ensuring proper seating of the inserter upon the implant, prevents damage to the inserter and implant. For example, the compression between the inserter and implant prevents any error in alignment between the two members. Thus, potential damage due to an offset or due to a spacing between the inserter and implant is minimized. Also, because the impact forces are not directed to the rod, the risk that an implant should be removed as a result of a broken rod is substantially reduced.

Furthermore, the inserters according to the invention reduce complications during surgery and risk to the patient. As discussed above, the inserters should result in less damage to the rod, other portions of the inserters, and to the implant. The inserters therefore reduce the chance that a damaged implant will have to be removed and replaced with a new implant. The inserters also eliminate the need for the surgeons to repeatedly monitor tension of the rod. Instead, the surgeons can focus on the surgical procedure, such as inserting the implant or instrument to the desired location. The inserters therefore require less oversight during use and should allow surgeons to more efficiently and easily drive implants to their desired locations.

The foregoing description of the preferred embodiments of the invention has been presented only for the purpose of illustration and description and is not intended to be exhaustive or to limit the invention to the precise forms disclosed. Many modifications and variations are possible in light of the above teaching. The embodiments were chosen and described in order to explain the principles of the invention and their practical application so as to enable others skilled in the art to utilize the invention and various embodiments and with various modifications as are suited to the particular use contemplated.

We claim:

1. A device for moving an object to a desired position, comprising:

a frame member having a receiving surface for receiving a force and a load transfer surface for contacting the object, the frame member for transferring the force from the receiving surface, to the load transfer surface, and then to the object;

an engagement member for securing the frame member to the object and for positioning the load transfer surface of the frame member against the object; and a biasing member for use in producing a compressive force between the load transfer surface and the object;

wherein the compressive force produced with the biasing member maintains contact between the load transfer surface and the object while the force is being applied to the receiving surface of the frame member.

2. The device according to claim 1, wherein the biasing member has a first position where the compressive force is not produced and a second position where the compressive force is produced, the device further comprising a locking member for locking the biasing member in the second position.

3. The device according to claim 1, further comprising the object.

4. The device according to claim 3, wherein the object comprises a prosthetic implant.

5. The device according to claim 4, wherein the implant comprises a femoral implant.

6. The device according to claim 4, wherein the implant comprises an acetabular cup.

7. The device according to claim 3, wherein the object comprises a broach.

8. The device according to claim 3, wherein the object comprises a reamer.

9. The device according to claim 3, wherein the object comprises an alignment tool.

10. The device according to claim 3, wherein the object comprises a depth guide.

11. The device according to claim 3, wherein the object comprises a gauge.

12. The device according to claim 1, wherein the load transfer surface comprises feet which contact the object.

13. The device according to claim 1, wherein the biasing member comprises a compression spring.

14. The device according to claim 1, wherein the engagement member comprises a threaded rod.

15. The device according to claim 1, wherein the frame member and the engagement member form an interface for being connected to the object.

16. The device according to claim 2, wherein the locking member comprises a lever.

17. The device according to claim 2, wherein the locking member comprises a thumbscrew.

18. A method of moving an object to a desired position, comprising attaching an insertion device to an object to be inserted;

positioning a load transfer surface of the insertion device against the object;

compressing the load transfer surface of the insertion device with the object; and transferring forces through the inserter to the object for directing the object to a desired position.

19. The method of claim 18, wherein the attaching comprises threading an engagement member into the object.

20. The method of claim 18, further comprising retaining the insertion device in place with a biasing member having first and second positions.

* * * * *